United States Patent
Baba

(10) Patent No.: US 7,314,541 B2
(45) Date of Patent: Jan. 1, 2008

(54) ION MEASURING COMPOSITE ELECTRODE

(75) Inventor: Toshiyuki Baba, Kyoto (JP)

(73) Assignee: Horiba, Ltd., Kyoto (JP)

( * ) Notice: Subject to any disclaimer, the term of this patent is extended or adjusted under 35 U.S.C. 154(b) by 757 days.

(21) Appl. No.: 10/695,298

(22) Filed: Oct. 28, 2003

(65) Prior Publication Data

US 2004/0129563 A1 Jul. 8, 2004

(30) Foreign Application Priority Data

Oct. 30, 2002 (JP) .............................. 2002-316611

(51) Int. Cl.
*G01N 27/333* (2006.01)
*G01N 27/36* (2006.01)

(52) U.S. Cl. ..................... 204/416; 204/420; 204/435

(58) Field of Classification Search ................. 65/33.5, 65/36, 40–42, 48, 57–58, 59.2, 59.27, 59.28, 65/59.35, 59.6, 152, 153, 155; 204/416, 204/435, 420

See application file for complete search history.

(56) References Cited

U.S. PATENT DOCUMENTS

| | | | | |
|---|---|---|---|---|
| 3,666,651 A | * | 5/1972 | Makabe ....................... 204/420 |
| 3,741,884 A | * | 6/1973 | Deushane et al. ........... 204/420 |
| 3,855,095 A | * | 12/1974 | Leonard et al. .............. 204/420 |
| 3,957,612 A | * | 5/1976 | Niedrach et al. ............ 204/414 |
| 4,128,468 A | * | 12/1978 | Bukamier ..................... 204/420 |
| 5,346,606 A | * | 9/1994 | Christner et al. ......... 205/787.5 |
| 6,054,031 A | * | 4/2000 | Benton ......................... 204/435 |
| 2003/0150726 A1 | * | 8/2003 | West et al. .................. 204/433 |

* cited by examiner

*Primary Examiner*—Kaj K. Olsen

(57) ABSTRACT

The present invention provides an improved ion measuring composite electrode, measuring instrument incorporating the composite electrode, and a manufacturing method for forming a preform of a composite double glass pipe for forming the ion measuring composite electrode. A hollow inner pipe and a hollow outer pipe are axially aligned with an elongated member having liquid absorption capacity. The inner pipe is welded to the outer pipe to form an annular space there between for receiving reference electrode liquid. The elongated member insures electrical conductivity even in the presence of air bubbles so that the measuring instrument is operatable and an appropriate weld can be easily manufactured to improve productivity.

31 Claims, 5 Drawing Sheets

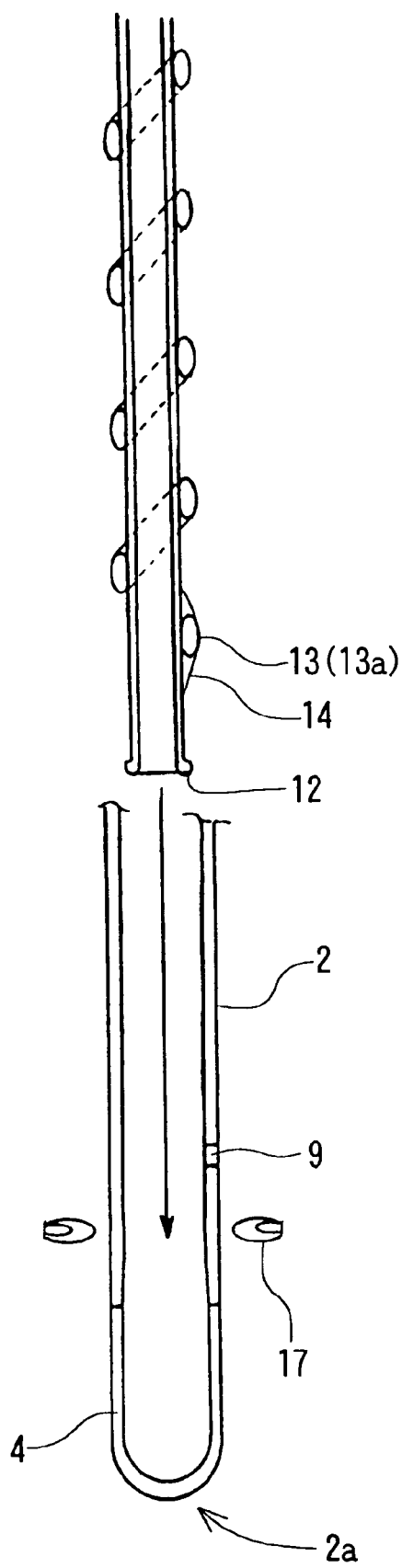
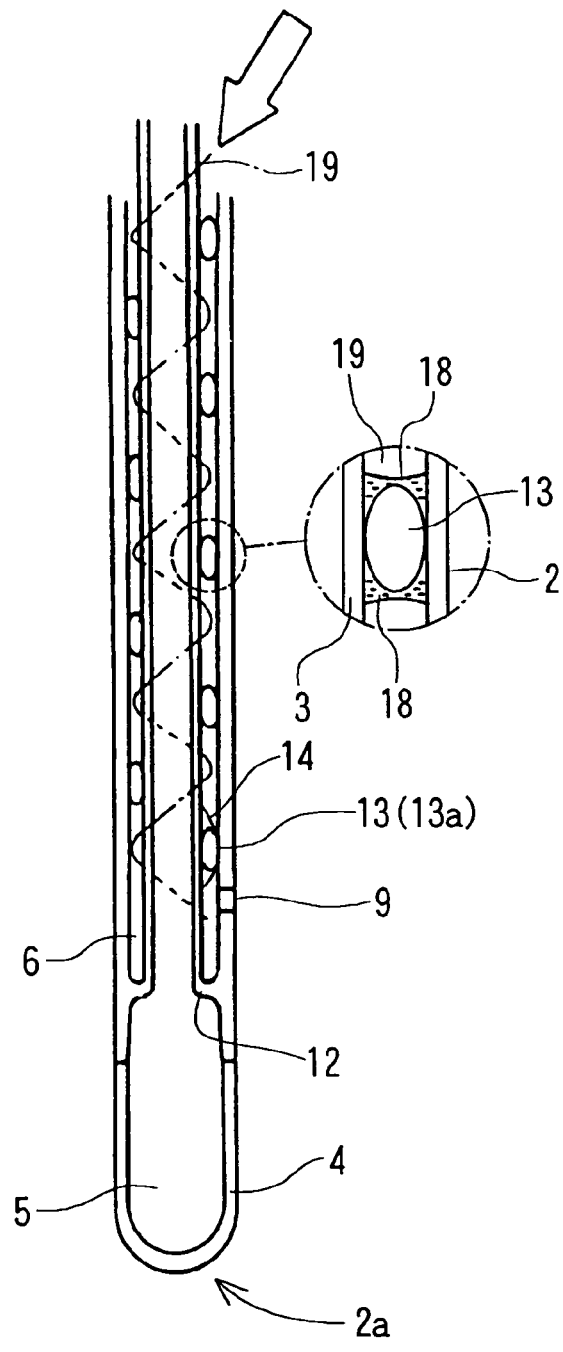

ION MEASURING COMPOSITE ELECTRODE

BACKGROUND OF THE INVENTION

1. Field of the Invention

The present invention relates to an improved ion measuring composite electrode, a measuring instrument incorporating such a composite electrode, and manufacturing method for a double glass pipe.

2. Description of Related Art

When measurement is performed for ion concentration of a sample, such as a pH value in a liquid, there has been used an ion measuring composite electrode constructed, as an integral one piece of a glass pipe serving as a measuring electrode and a glass pipe installed for a reference electrode. Generally, since an ion measuring composite electrode is relatively complicated in structure the resulting electrode can be relatively large in size, and it is difficult to manufacture an equivalent electrode that is small in size.

FIG. 4 is a schematic view showing a construction of a pH composite electrode 20 employing a double pipe structure, in which a responsive section for an ion concentration, such as a pH value, is formed as a long and narrow channel, and which has been developed to enable an ion concentration of a very small amount of a solution, such as a measuring specimen, to be measured. Furthermore, FIGS. 5A and 5B are views describing a manufacturing method for this type of double pipe structure.

In FIGS. 4, and 5A and 5B, a numerical symbol 2 denotes an outer pipe and 3 denotes an inner pipe of the double pipe structure. The outer pipe 2 is formed so that a distal end 2a thereof is sealed and is of an extremely narrow diameter, in the order of several mm, wherein a diameter of the proximal end 2b assumes a large value so as to be connectable to a body 20a side of the pH composite electrode 20. Furthermore, a pH responsive section 4 made from a glass that is responsive to an ion, such as a pH value, is provided at the distal end 2a of the outer pipe 2.

The distal end 3a of the inner pipe 3 is expanded at an outer diameter thereof and the expanded outer periphery is glass-welded to the inner peripheral surface of the outer pipe 2 to thereby create a separate space 5 in the interior of the inner pipe 3 for communicating with a pH responsive section 4. The space 5 extends through the inner pipe 3 from an annular space 6 formed between the outer pipe 2 and the inner pipe 3 with the result that a construction is formed so that the space 5 can be filled with a measuring electrode internal liquid 7 and the space 6 can be filled with a reference electrode internal liquid 8.

A liquid connecting section 9 made of a ceramic filling a small hole is formed in the outer pipe 2, and is located near the lower end of the annular space 6 to communicate with the outside of the outer pipe 2. An internal electrode 10 is immersed in a measuring electrode internal liquid 7 in the space 5, and a reference electrode 11 is immersed in the reference electrode internal liquid 8 in the space 6. Therefore, when a pH composite electrode 20 is constructed, a measurement of a pH value is enabled for even a very small amount of a measuring specimen when the liquid connecting section 9 and the pH responsive section 4 is immersed in the solution, as a measuring specimen.

In the fabrication of a double pipe structure with the outer pipe 2 and the inner pipe 3, as shown in FIG. 5A, a technique has been adopted in a prior art practice where the opening at the distal end 3a of the inner pipe 3 is expanded so that the outer periphery of the opening becomes close to the inner peripheral surface of the outer pipe 2 to form a flange section 12. The inner pipe 3 thus worked is inserted into the outer pipe 2 with the distal end 3a as a leading head. At this time, the proximal end 3b of the inner pipe 3 is carefully fixed with a bushing or the like (not shown) so that the distal end 3a is aligned with the outer pipe 2a with respect to the center axes. Then, heat is applied on the outer peripheral surface of the outer pipe 2 using a gas burner 17 while rotating the outer and inner pipes 2 and 3 using a lathe or the like to thereby weld the flange section 12 to the inner peripheral surface of the outer pipe 2.

In such a welding, however, a problem of a defective welding has arisen as shown in FIG. 5B since the inner pipe 3 can move to create a positional instability in the outer pipe 2 so that the outer pipe 2 and the inner pipe 3 are insufficiently aligned with each other with respect to the center axes at the distal ends 2a and 3a thereof.

Also a problem of transferring more heat than necessary from the gas burner 17 to the flange section 12 in those portions where the inner pipe 3 is closer to the outer pipe 2 can occur, which can cause fusion of the glass over a wide range to cause the outer pipe 2 to be placed in wide contact with the inner pipe 3 in a portion 12a apart from a target portion. Additionally, in those portions where the inner pipe 3 is positioned farther away from the outer pipe 2, welding can produce a clearance 12b, which can permit the spaces 5 and 6 to communicate with each other. This problem can occur since heat from the gas burner 17 is hard to be transferred to the flange section 12.

In addition, since the outer and inner pipes 2 and 3 are formed in an extremely narrow offset, difficulty has accompanied the aligning of both the center axes. That is, not only is there a shift in a center axis between the distal ends 2a and 3a which is hard to visually recognize from outside the outer pipe 2, but difficulty also arises in visual judgment on a value of a force imposed on a site where the flange section 12 is in contact with the inner peripheral surface of the outer pipe 2, if any. Hence, even though the welding work is done with deliberate attention thereto and with extra time, a case can arise where a shift between the center axes is occurs, and defective weld happens, resulting in a poor production rate.

Moreover, a necessity exists for the interiors of the inner and outer pipes of the formed double pipe structure to be completely filled with an internal liquid, and with a decrease in diameters of the outer and inner pipes 2 and 3, the space 6, which is the gap between the outer and inner pipes 2 and 3, can become too narrow; therefore, the reference electrode internal liquid 8 can be difficult to evenly spread within the space 6 to every part thereof and a bubble can be produced between the reference electrode 11 and the liquid connecting section 9 to cause an electrically open state, leading to a problem of disabling a measurement. In a case where the reference electrode internal liquid 8 decreases, a bubble can also be incorporated into the space 6 when the reference electrode internal liquid is supplemented.

Thus the prior art is still seeking both an improved method of manufacturing concentric small diameter glass tubes and a resultant improved ion measuring composite electrode with improved production rates.

SUMMARY OF THE INVENTION

The present invention has been made in light of the above circumstances and it is an object of the present invention to provide a manufacturing method for a double glass pipe and an ion measuring composite electrode, not only making it easy to manufacture a glass composite pipe of a double structure for constructing an ion measuring composite electrode, but also capable of insuring a setoff space between an outer glass pipe and an inner glass pipe of a formed double structure is electrically conductive even if the presence of a bubble occurs in the space.

In order to achieve the above object, a manufacturing method for a composite double glass pipe of the present invention is characterized by an inner pipe and an outer pipe having a diameter whose lower section is designed so as to be narrower than that of the proximal end thereof, an opening at the distal end of the inner pipe is expanded so that the outer periphery of the opening becomes close to the inner peripheral surface of the outer pipe, a string-like or elongated member is wound on an outer peripheral surface of the inner pipe such as in the form of a spiral and the inner pipe is inserted into the outer pipe while holding a constant spacing between the inner pipe and the outer pipe around the inner pipe, and thereafter, the distal end of the inner pipe is welded to the inner peripheral surface of the outer pipe.

Therefore, the string-like member, wound on the outer peripheral surface of the inner pipe, can be elastically deformed and simultaneously brought into contact with the outer peripheral surface of the inner pipe and the inner peripheral surface of the outer pipe to thereby impose a force uniformly in every direction so as to expand a gap between the inner pipe and the outer pipe, thereby enabling neither play nor positional instability between the inner pipe and the outer pipe to occur. The gap between the inner pipe and the outer pipe is held at a constant value around the inner pipe with the help of the string-like member. That is, when the distal end of the inner pipe is welded to the outer pipe, the centers of the distal ends of the inner pipe and the outer pipe can be aligned with each other precisely. Furthermore, a worker can perform such centering between the inner pipe and the outer pipe with extreme ease and quickness with a result of effectively preventing any fusion over a wide range which can cause the outer pipe to be put into wide contact with the inner pipe in a portion except for a target region to be welded, thereby enabling a formation of a glass pipe in a double structure with a good production yield.

As a string-like member, there can be used, for example, a string such as a cotton string. A string capable of being elastically deformed to a predetermined extent is desirable in order to perform centering between the inner pipe and the outer pipe, and a string can employ other kinds of materials with sufficient elasticity and high water absorption capacity, for example rubber and sponge, both having being water absorption-treated, and having communicating air bubbles therein, and in addition, a net tube and water absorbing tube.

An ion measuring composite electrode of the present invention can include an outer pipe in which not only is a distal end thereof closed, but a diameter of a lower section is also narrower than that of a proximal end thereof, and which includes an ion responsive section and a liquid connecting section; an inner pipe in which a distal end thereof is welded to an inner peripheral surface of the outer pipe in a state where the inner pipe is inserted in the outer pipe to thereby form an annular space between the outer pipe and the inner pipe; and a string-like member, having a water absorption capacity, and disposed in the annular space in a state where the string-like member is wound on the inner pipe.

The string-like member having sufficient water absorption capacity is located in the annular space between the inner pipe and the outer pipe and thereby can absorb an internal liquid. With such a nature of the member, even if an air bubble is mixed into the annular space, electrical conduction through the space is still secured by transmission through the string-like member, which can serve as a salt bridge, in a practical sense, thereby enabling a measurement. Furthermore, it is possible to secure a flow path filled with the internal liquid in which the internal liquid is easy to flow through the string-like member, making it easy for the internal liquid to prevail in a narrow gap to every part thereof.

In addition thereto, since the string-like member works as a spacer between the outer pipe and the inner pipe because of its location in the annular space between the inner pipe and the outer pipe, the string-like member can contribute to an improvement in durability in even a double glass pipe structure formed in an extremely narrow way so as to enable a measurement of an ion concentration in a very small amount of a solution, as a measuring specimen. That is, there can be formed an ion measuring composite electrode excellent in durability, though it is small-sized by supporting the glass pipes and absorbing shock energy.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIGS. 3A and 3B are views disclosing a manufacturing method for a double glass pipe and workings thereof;

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the intention is intended to cover alternatives, modifications and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and circuits have not been described in detail as not to unnecessarily obscure aspects of the present invention. For example, details of a measuring instrument with a composite electrode are known and shown in FIG. 4 and accordingly only the improved elements are set forth herein.

A description will now be given of details of the invention below with reference to the accompanying drawings.

Figure 1:
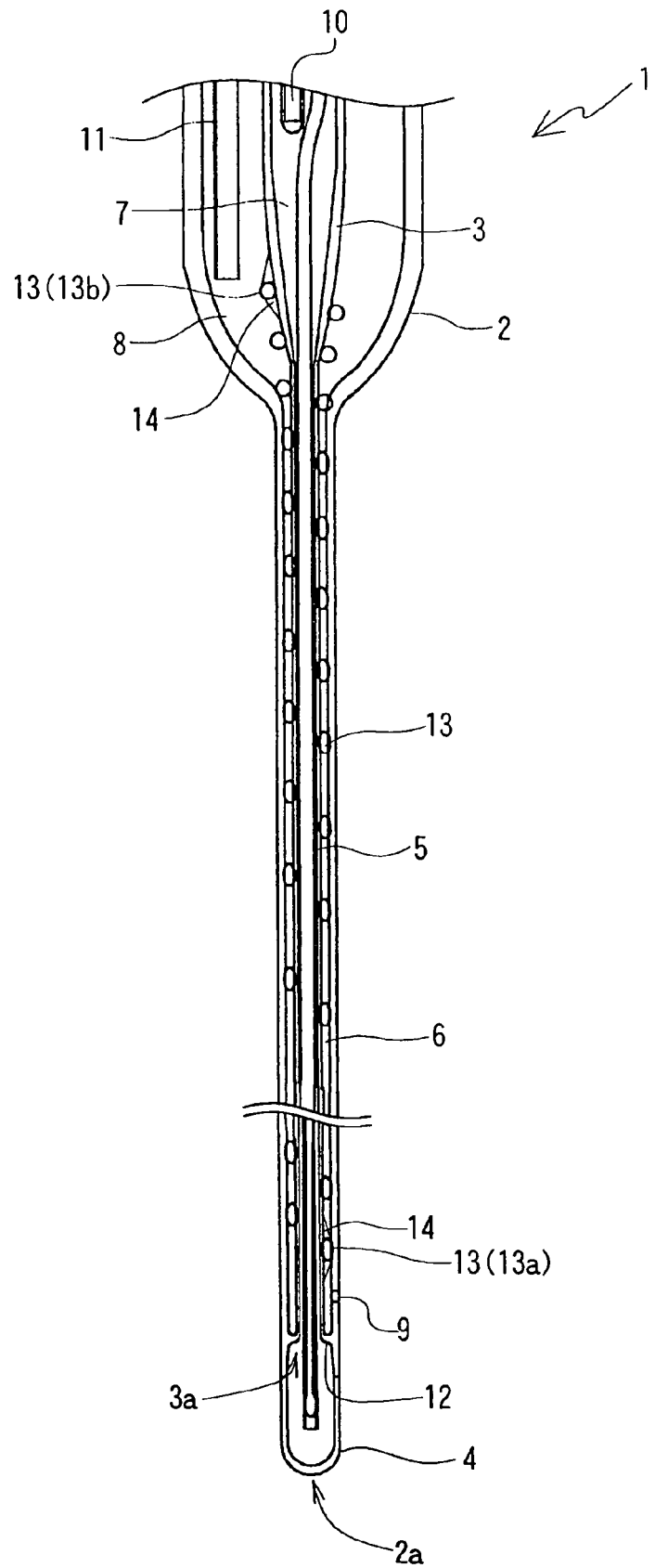
FIG. 1 is a view showing a construction of an ion measuring composite electrode of the present invention.
Figure 2:
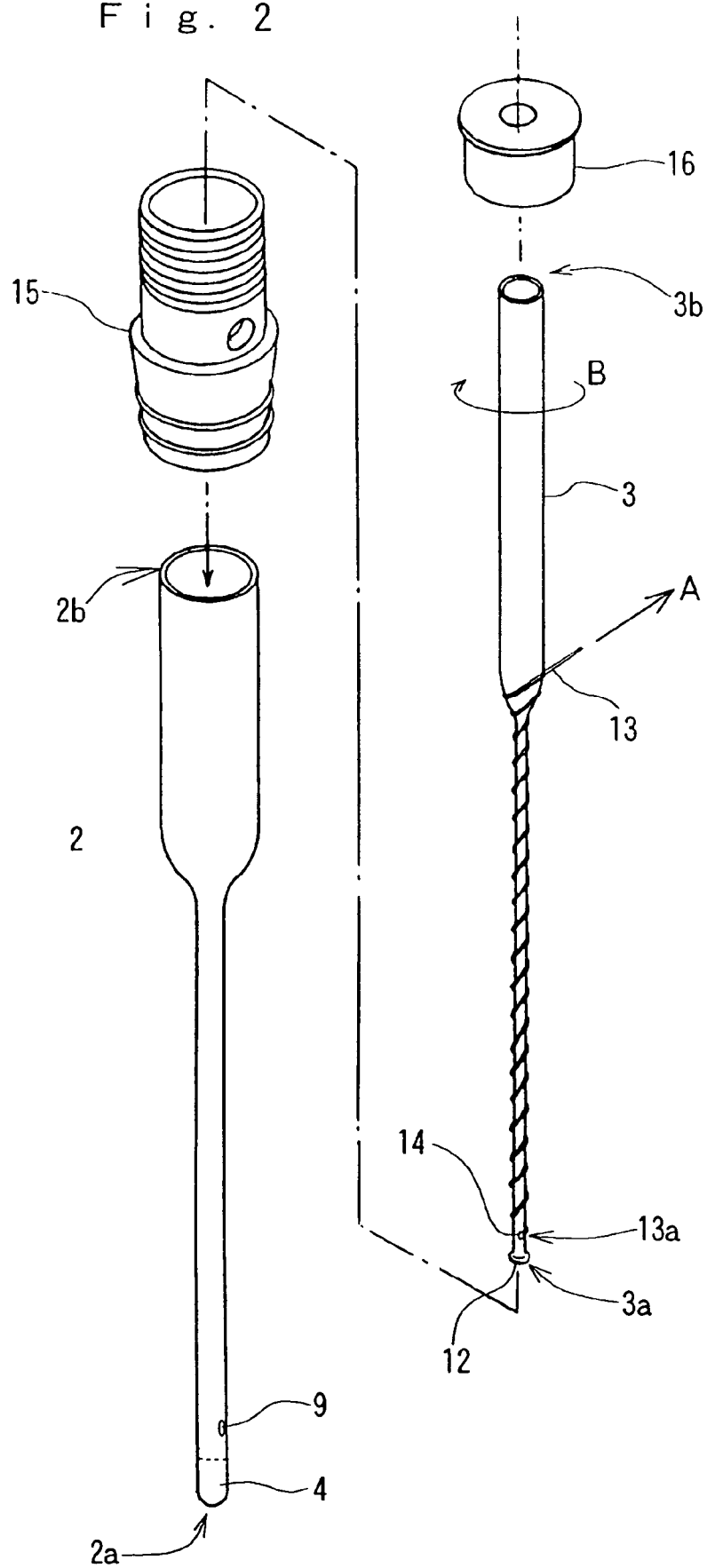
FIG. 2 is an exploded perspective view of a double glass pipe structure of the ion measuring composite electrode.
Figure 4:
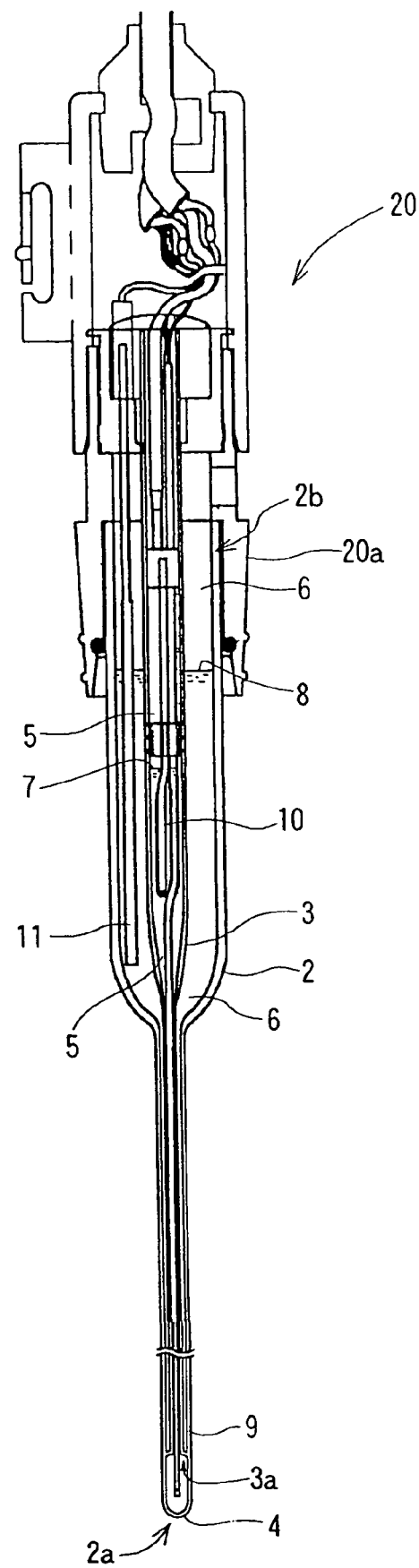
FIG. 4 is a view showing a construction of a prior art ion measuring composite electrode.
Figure 5A:
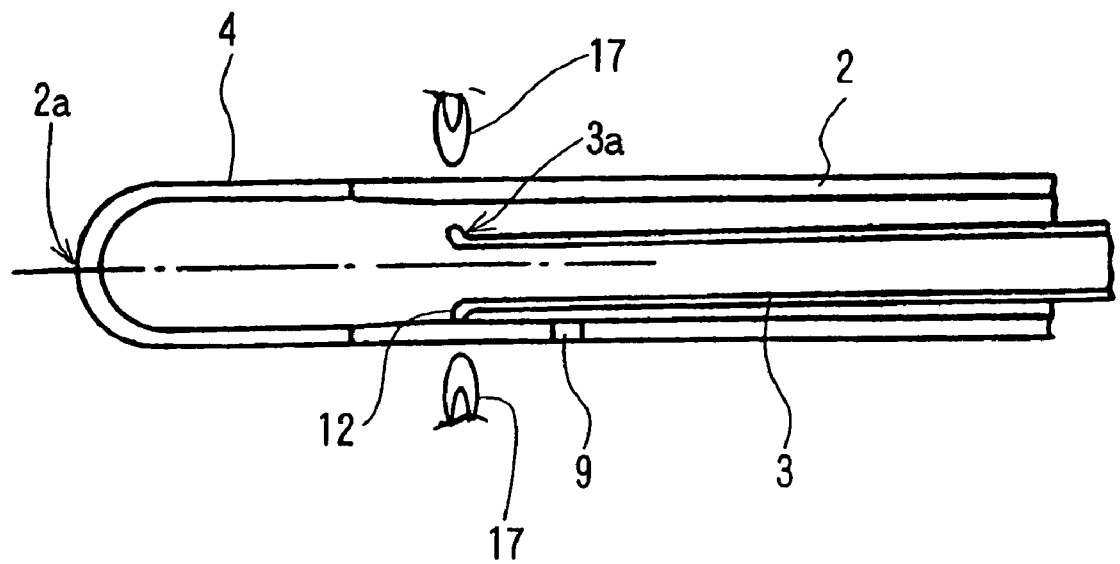
FIGS. 5A and 5B are views describing a manufacturing method for a double glass pipe structure of a prior art ion measuring composite electrode.
Figure 5B:
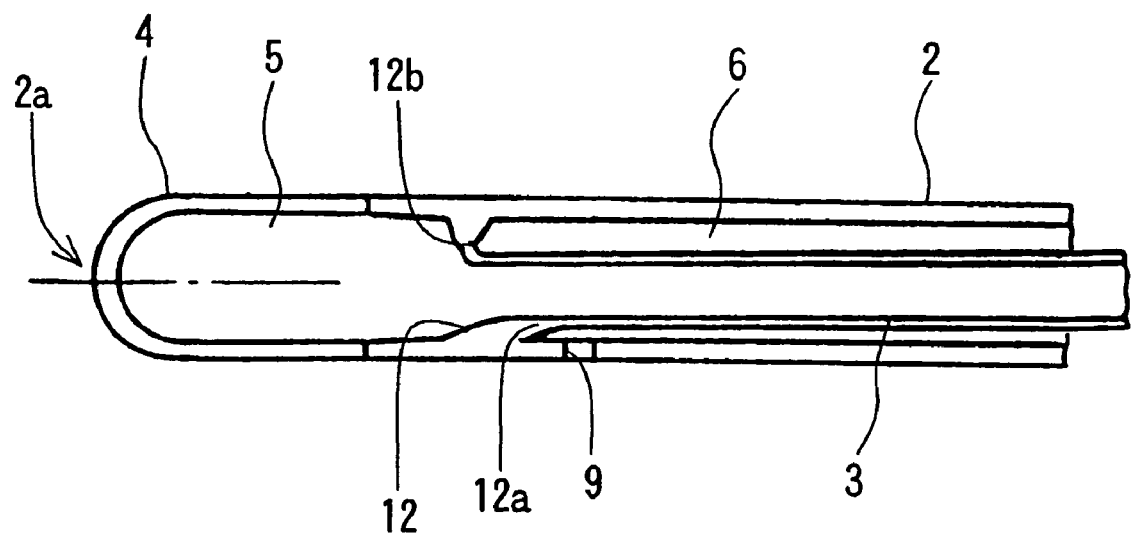

FIG. 1 is a view showing one example of a construction of an ion measuring composite electrode 1 (in this example, a pH composite electrode) of an extremely narrow type according to the present invention. FIG. 2 and FIGS. 3A and 3B are views describing a manufacturing method for the pH composite electrode 1. In FIGS. 1, 2, and 3A and 3B, constituents denoted with the same symbols as respective constituents in FIGS. 4 and 5 are equivalent to the respective constituents in FIGS. 4 and 5, and as such, detailed descriptions thereof are not repeated.

In a pH composite electrode 1 of the present invention, an elongated or a string-like member 13 with a water absorption capacity and a pre-determined elasticity is wound on an outer peripheral surface of the inner pipe 3, for example, in the form of a spiral. Alternatively, other elongated material with sufficient water absorption capacity including sponge material can be used. The form of the member 13 can be altered to be a tube or an elongated net configuration to provide both spacing and liquid retention.

As string-like members 13 with a water absorption capacity and elasticity, there can be exemplified: a cotton string (a kite string) rich in hydrophlicity and with a proper elasticity slightly thicker than a gap between the outer pipe 2 and the inner pipe 3.

An adhesive 14 adhering to an end 13a of the cotton string 13 is positioned in the vicinity of the distal end 3a of the inner pipe 3, such as a silicon resin (for example, made by Shin-Etsu Chemical Industry Co., Ltd. with a trade name of KE-66) without an influence or interference on an reference electrode internal liquid.

As a method of winding the cotton string 13, an end 13a of the cotton string 13 is attached to a position in the vicinity of the distal end 3a of the inner pipe 3 with the adhesive 14, and the inner pipe 3 is, as shown with an arrow symbol A in FIG. 2, rotated while pulling the inner pipe 3 toward the proximal end thereof with a proper force. The cotton string 13 is cut almost at a position past a section where a diameter of the inner pipe 3 increases to adhere the other end 13b to the side surface of the inner pipe 3.

Note that the end 13a of the cotton string 13 is desirably located at the closest possible point to the liquid connecting section 9 and the other end 13b is, while the inner pipe 3 is inserted into the outer pipe 2, desirably disposed at a position just past a section where the cotton string 13 is sandwiched between the inner pipe 3 and the outer pipe 2.

Not only is the inner pipe 3, on which the cotton string 13 is wound, assembled so as to be aligned with the outer pipe 2 to provide concentric circles at the proximal end using assembly caps 15 and 16 shown in FIG. 2, but also the inner pipe 3 is, as shown in FIG. 3A, inserted into the outer pipe 2 and thereby is brought into contact with the outer peripheral surface of the inner pipe 3 and the inner peripheral surface of the outer pipe 2 to slightly perform an elastic deformation of the cotton string 13. At this time, the inner pipe 3 is guided in the insertion while performing centering so as to align the center of the inner pipe 3 with the center of the outer pipe 2 with certainty by a elastic deformation of the cotton string 13.

Heat is then applied to a portion of the outer pipe 2 corresponding to the flange section 12 formed by expanding the opening of the distal end 3a of the inner pipe 3 so as to be close to the inner peripheral surface of the outer pipe 2. The heat can be applied from the gas burner 17 or the like to an outer peripheral surface of the outer pipe 2, thereby enabling the flange section 12 to be welded to the outer pipe 2.

At this time, since the centers of the outer and inner pipes 2 and 3 are aligned with certainty through the elastic deformation of the cotton string 13, no unbalanced transfer of heat occurs in the welding of the flange section 12 and the flange section 12 is properly welded at its outer periphery to the inner peripheral surface of the outer pipe 2. A controlled separation can accordingly be realized between the space 5 in the inner pipe 3 and the annular space (gap) 6 sandwiched between the inner pipe 3 and the outer pipe 2.

In a pH composite electrode 1 manufactured with this type of preform of composite glass tubes, the space in the inner pipe 3 is filled with a glass electrode internal liquid 7 and the annular space 6 is filled with the reference electrode internal liquid 8.

At this time, since the reference electrode internal liquid 8 is not only absorbed in the bulk of the cotton string 13, but also is attached to a peripheral surface thereof. A flow path 18 (see an enlarged view) in the form of a spiral filled with the reference electrode internal liquid 8, as shown in FIG. 3B, is formed around the cotton string 13 by a surface tension of the liquid. On the other hand, a discharge path 19 in the form of a spiral of air bubbles may be formed between pairs of windings of the cotton string 13. That is, a pH composite electrode 1 of the present invention is wound with the cotton string 13 in the form of a spiral to thereby not only facilitate the reference electrode internal liquid 8 to be introduced into the annular space 6 in the double pipe formed in an extremely narrow way, but also to facilitate positioning air bubbles in the space 6, if any is mixed therein.

Even if air bubbles are mixed into the space 6, the flow path 18 filled with the internal liquid absorbed into the cotton string 13 and positioned around the periphery can serve as a salt bridge; therefore, no electric conduction is disconnected because of the location of bubbles, if any, between the liquid connecting section 9 and the reference electrode 11. Therefore, if a bubble or bubbles are mixed into the space 6 by tilting the pH composite electrode 1 in a situation with a small amount of the reference electrode internal liquid 8 remaining therein, the measurement won't be disabled.

While in the examples, the double pipe structure is part of the pH composite electrode 1 having the pH responsive section 4 formed at the distal end, the present invention is not limited to a measurement on a pH value. The present invention can also apply to an ion measuring composite electrode with an ion responsive section suitable for measuring a concentration of any of a variety of various kinds of ions in a similar manner. Furthermore, in the above example, the electrode construction is exemplified in which the ion responsive section 4, exposed to the space 5, is formed at the distal end 2a of the outer pipe 2 and the liquid connecting section 9 is formed in a portion communicating with the annular space 6 in the vicinity of the ion responsive section 4, According to the present invention, not only is the manufacturing of a pH composite electrode 1 facilitated with a better product yield, but also a pH composite electrode 1 can be formed with adaptability even for the case of a mixing-in of air bubbles through a salt bridge effect by the cotton string 13 and therefore, a higher reliability. Note that by providing the shape of a string of almost uniform thickness and elasticity, the string-like member 13 is particularly suited for positioning of the inner pipe 3 with the outer pipe 2 with respect to the centers (centering), but the string-like member is not necessarily limited to natural or artificial fibers as a material and various modifications such as an elongated sponge can be considered.

While an elastic force of the string-like member 13 is desirably strong in order to assist positioning of the inner pipe 3 within the outer pipe 2 and further improves durability, various other kinds of material can be employed as long as the material does not adversely influence the internal liquid 8. In addition, considering the welding of the flange section 12, a certain degree of heat resistance is desirably imparted to the string-like member 13.

Likewise, as long as the elongated or string-like member 13 is made of a material rich in water absorption capacity and hydrophilicity and can function as a salt bridge, there is no necessity that the string-like member be limited to fabric.

Furthermore, in order to perform sufficient centering of the inner pipe 3 with the outer pipe 2, it is desirable that the string-like member 13 is densely wound in the form of a spiral, while in order to perform attraction and absorption of the internal liquid 8, and removal of bubbles, it is desirable that the string-like member 13 is sparsely wound. Accordingly, in winding of the string-like member 13 described in FIG. 2, a possible modification can be considered where the string-like member 13 is densely wound at the distal end 3a and more sparsely wound toward the proximal end.

Moreover, the string-like member 13 can be comparatively densely wound in a first stage operation and when welding of the flange section 12 is completed, a density of the windings of the string-like member 13 is reduced by pulling it off the inner pipe 3, thereby enabling the windings to be sparse.

With implementation of the present invention, precise centering can be ensured in welding glass pipes into a double structure, and a construction is obtained with a positional stability between the outer and inner pipes. Additionally, fusion over a wide contact area in portions different from a target portion can be prevented with the result of a better product yield and improvement of productivity. Since there is provided a string-like member with a water absorption capability between the inner pipe and the outer pipe, the internal liquid can be easily spread through the gap to every part thereof and even in a case where a bubble or bubbles are generated between the internal electrode and the liquid connecting section, the electric conduction is ensured, thereby enabling a measurement on an ion concentration.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

What is claimed is:

1. An ion measuring composite electrode comprising:
    an outer pipe having a closed distal end with a diameter of a portion adjacent the distal end narrower than a proximal end thereof;
    an ion responsive section and a liquid connecting section is provided on the outer pipe; and
    an inner pipe is provided within the outer pipe and is spaced from the outer pipe by a string-like member with liquid absorption characteristics to form an annular space for providing a space for a reference liquid, the inner pipe is connected to the outer pipe to form the annular space and the string-like member is spirally wound around the inner pipe.

2. The ion measuring composite electrode of claim 1 wherein the elongated member is a string wound around the inner pipe.

3. The ion measuring composite electrode of claim 2 wherein the outer pipe and inner pipe are glass that are connected together by welding.

4. The ion measuring composite electrode of claim 2 wherein a cotton string is wound spirally around the inner pipe.

5. In an improved measuring instrument for measuring a liquid specimen, the improvement comprising:
    a composite electrode including an inner pipe spaced by a string-like member wrapped around the inner pipe for offsetting a surrounding hollow outer pipe, the inner pipe is welded to the outer pipe to provide an annular space between the inner and outer pipe for receiving a reference electrode liquid, the string-like member has liquid absorption characteristics.

6. The improved measuring instrument of claim 5 wherein the elongated member is a string having hydrophilicity for a reference electrode liquid.

7. The improved measuring instrument of claim 6 wherein the elongated member is compressed between the inner pipe and the outer pipe to concentrically aligned respective axes of the inner pipe and outer pipe.

8. An ion measuring composite electrode comprising:
    an inner hollow glass pipe;
    an outer hollow glass pipe having an inner surface cross sectional dimension greater than an outer surface cross sectional dimension of the inner hollow glass pipe, wherein the inner hollow glass pipe is positioned within the outer hollow glass pipe;
    a string-like member, having a characteristic of liquid absorption, is positioned between the inner surface of the outer hollow glass pipe and the outer surface of the inner hollow glass pipe to space the inner hollow glass pipe from the outer hollow glass pipe, wherein the inner hollow glass pipe outer diameter is sealed to the inner diameter of the outer hollow glass pipe to form a reference electrode internal liquid space and the string-like member is spirally wound around the inner hollow glass pipe;
    a liquid connecting section is provided adjacent one end of the outer hollow glass pipe to communicate with the sealed reference electrode internal space between the inner hollow glass pipe and the outer hollow glass pipe;
    a reference electrode internal liquid is in the sealed reference electrode internal spacer;
    a reference electrode communicates with the sealed reference electrode internal spacer;
    a measuring electrode internal liquid is within the hollow inner glass pipe;
    an internal electrode communicates with the inner hollow glass pipe; and
    an ion responsive section is provided on the outer hollow glass pipe.

9. The ion measuring composite electrode of claim 8 wherein the string-like material is a water absorption material.

10. The ion measuring composite electrode of claim 9 wherein the string-like material is an elongated material wound around the inner hollow glass pipe.

11. The ion measuring component electrode of claim 10 wherein the string-like material is helically wound between the inner glass pipe and the outer hollow glass pipe.

12. The ion measuring composite electrode of claim 11 wherein the sting-like material is adhered adjacent one end of the inner hollow glass pipe.

13. The ion measuring composite electrode of claim 12 wherein the inner hollow glass pipe is annularly welded at one end to the outer hollow glass pipe.

14. The ion measuring composite electrode of claim 8 wherein the outer hollow glass pipe has an enlarged inner diameter at one end and the inner glass pipe has an enlarged outer diameter positioned within the enlarged inner diameter.

15. The ion measuring composite electrode of claim 14 further including a first assembly cap attached to the outer hollow glass pipe and a second assembly cap mounted within the first assembly cap and attached to the inner hollow glass pipe.

16. The ion measuring composite electrode of claim 8 wherein the string-like material is selected from one of sponge, rubber and an elongated cotton string.

17. The ion measuring composite electrode of claim 16 wherein the cotton string is wound around an outer peripheral surface of the inner hollow glass pipe to both space the outer hollow glass pipe from the inner hollow glass pipe and to provide electrical conductivity in the presence of any bubble in the reference electrode internal liquid.

18. An ion measuring composite electrode comprising:
an inner hollow glass pipe;
an outer hollow glass pipe having an inner surface cross sectional dimension greater than an outer surface cross sectional dimension of the inner hollow glass pipe, wherein the inner hollow glass pipe is positioned within the outer hollow glass pipe;
a water absorbing flexible string-like member is positioned between the inner surface of the outer hollow glass pipe and the outer surface of the inner hollow glass pipe to space the inner hollow glass pipe from the outer hollow glass pipe, wherein the inner hollow glass pipe outer diameter is sealed to the inner diameter of the outer hollow glass pipe to form a reference electrode internal liquid space and the string-like member is spirally wound around the inner hollow glass pipe;
a liquid connecting section is provided adjacent one end of the outer hollow glass pipe to communicate with the sealed reference electrode internal space between the inner hollow glass pipe and the outer hollow glass pipe;
a reference electrode internal liquid is in the sealed reference electrode internal spacer;
a reference electrode communicates with the sealed reference electrode internal spacer;
a measuring electrode internal liquid is within the hollow inner glass pipe;
an internal electrode communicates with the inner hollow glass pipe; and
an ion responsive section is provided on the outer hollow glass pipe, wherein the outer hollow glass pipe has an enlarged inner diameter at one end and the inner hollow glass pipe has an enlarged outer diameter positioned with the enlarged inner diameter when compared to the inner and outer diameter adjacent the ion responsive section.

19. The ion measuring composite electrode of claim 18 wherein the string-like member is a cotton string.

20. The ion measuring composite electrode of claim 19 wherein the cotton string is adhered with an adhesive material to the outer surface of the inner hollow glass pipe adjacent a liquid connecting section on the outer hollow glass pipe and the cotton string is spirally wound around the inner hollow glass pipe and compressed against the inner surface of the outer hollow glass pipe, wherein the cotton string stops being spirally wound around the inner hollow glass pipe adjacent the reference electrode.

21. In an improved measuring instrument for measuring a liquid specimen, a reference electrode internal liquid, the improvement comprising:
a composite electrode including an inner glass pipe and an outer glass pipe, the inner glass pipe is integrally connected adjacent one end of the outer glass pipe and cantilevered towards another end of the outer glass pipe from the integral connection to contain the reference electrode internal liquid between an outer surface of inner glass pipe and an inner surface of the outer glass pipe; and
means for preventing a disconnect in electrical conduction of the reference electrode internal liquid by any formation of bubbles in the reference electrode internal liquid between the surface of the inner glass pipe and the surface of the outer glass pipe including an elongated member with hydrophilicity for the reference electrode internal liquid extending between and intermittently contacting the outer surface of the inner glass pipe and the inner surface of the outer glass pipe.

22. The improved measuring instrument of claim 21 wherein the elongated member is a string-like member.

23. The improved measuring instrument of claim 22 wherein the elongated member is a string helically wound around the outer surface of the inner glass pipe and sandwiched against the inner surface of the outer glass pipe.

24. An ion measuring composite electrode comprising:
an inner hollow glass pipe;
an outer hollow glass pipe having an inner surface cross sectional dimension greater than an outer surface cross sectional dimension of the inner hollow glass pipe, wherein the inner hollow glass pipe is positioned within the outer hollow glass pipe and integrally interconnected at one end of the inner hollow glass pipe to be cantilevered co-axially within the outer hollow glass pipe to form an annular internal spacer for a reference electrode internal liquid between the inner surface of the outer hollow glass pipe and the outer surface of the inner hollow glass pipe;
a liquid connecting section is provided adjacent one end of the outer hollow glass pipe to communicate with the sealed reference electrode internal space between the inner hollow glass pipe and the outer hollow glass pipe and a sample specimen exterior to the outer glass pipe;
a reference electrode internal liquid is in the sealed reference electrode internal spacer;
a reference electrode communicates with the sealed reference electrode internal spacer;
a measuring electrode internal liquid is within the hollow inner glass pipe;
an internal electrode communicates with the inner hollow glass pipe;
an ion responsive section is provided on the outer hollow glass pipe; and
a flexible reference electrode internal liquid absorbing material is positioned between the inner surface of the outer hollow glass pipe and the outer surface of the inner hollow glass pipe to space the inner hollow glass pipe from the outer hollow glass pipe, and to provide a linear conductive path from the liquid connecting section through the annular internal space with the reference electrode internal liquid and to provide a flexible support between the outer hollow glass pipe and the inner hollow glass pipe.

25. The ion measuring composite electrode of claim 24 wherein the flexible material is an elongated material wound around the inner hollow glass pipe.

26. The ion measuring component electrode of claim 25 wherein the flexible material is helically wound between the inner glass pipe and the outer hollow glass pipe.

27. The ion measuring composite electrode of claim 24 wherein the flexible material is adhered adjacent one end of the inner hollow glass pipe adjacent the liquid connecting section.

28. The ion measuring composite electrode of claim 24 wherein the outer hollow glass pipe has an enlarged inner diameter at one end and the inner glass pipe has an enlarged outer diameter positioned within the enlarged inner diameter.

29. The ion measuring composite electrode of claim 28 further including a first assembly cap attached to the outer hollow glass pipe and a second assembly cap mounted within the first assembly cap and attached to the inner hollow glass pipe.

30. The ion measuring composite electrode of claim 24 wherein the flexible material is an elongated cotton string.

31. The ion measuring composite electrode of claim 30 wherein the cotton string is wound around an outer peripheral surface of the inner hollow glass pipe to both space the outer hollow glass pipe from the inner hollow glass pipe and to provide electrical conductivity in the presence of any bubble in the reference electrode internal liquid.

* * * * *